US010786651B2

(12) United States Patent
Edminster et al.

(10) Patent No.: US 10,786,651 B2
(45) Date of Patent: Sep. 29, 2020

(54) STEERABLE GUIDE CATHETER

(71) Applicant: Talon Medical, LLC, Salt Lake City, UT (US)

(72) Inventors: Darren Edminster, Brooklyn Park, MN (US); Douglas Wahnschaffe, Brooklyn Park, MN (US); Steve Berhow, Brooklyn Park, MN (US)

(73) Assignee: Talon Medical, LLC, Salt Lake City, UT (US)

( * ) Notice: Subject to any disclaimer, the term of this patent is extended or adjusted under 35 U.S.C. 154(b) by 388 days.

(21) Appl. No.: 15/452,675

(22) Filed: Mar. 7, 2017

(65) Prior Publication Data

US 2018/0256851 A1 Sep. 13, 2018

(51) Int. Cl.
*A61M 25/01* (2006.01)
*A61M 25/09* (2006.01)
*A61M 25/00* (2006.01)

(52) U.S. Cl.
CPC .... *A61M 25/0147* (2013.01); *A61M 25/0097* (2013.01); *A61M 25/0108* (2013.01); *A61M 25/0113* (2013.01); *A61M 25/0136* (2013.01); *A61M 25/09041* (2013.01); *A61M 2025/015* (2013.01)

(58) Field of Classification Search
CPC .......... A61M 25/0105; A61M 25/0133; A61M 25/0136; A61M 25/0147; A61M 2025/015; A61M 2025/0161; A61B 1/005; A61B 1/0051; A61B 1/0052; A61B 1/0053; A61B 1/0057; A61B 2017/003; A61B 2017/00318; A61B 2017/00323; A61B 2017/00327
See application file for complete search history.

(56) References Cited

U.S. PATENT DOCUMENTS 5,254,088 A * 10/1993 Lundquist ......... A61M 25/0144
600/585
5,441,483 A 8/1995 Avitall
5,462,527 A 10/1995 Wright et al.
(Continued)

FOREIGN PATENT DOCUMENTS

EP 0605796 A2 7/1994

OTHER PUBLICATIONS

International Searching Authority, International Search Report and Written Opinion of the International Searching Authority, International Application No. PCT/US2018/021418, dated May 15, 2018, 9 pages.

*Primary Examiner* — Kami A Bosworth
(74) *Attorney, Agent, or Firm* — Med Venture Management, LLC; Daniel C. Higgs

(57) ABSTRACT

A flexible guide tube having a deflectable distal end is disclosed with at least first and second tensioning lines coupled to a deflectable distal end of the flexible guide tube. The first tensioning line is configured to deflect the distal end of the flexible guide tube in a first direction and the second tensioning line is configured to deflect the distal end of the flexible guide tube in a second direction that is opposite the first direction. A handle is coupled to flexible tube, the handle having a medial portion with a longitudinal axis substantially parallel with at least a portion of the flexible guide tube, a first actuator disposed proximal the medial section, and a second actuator disposed distal the medial section.

35 Claims, 5 Drawing Sheets

(56) References Cited

U.S. PATENT DOCUMENTS

| | | |
|---|---|---|
| 5,823,955 A | 10/1998 | Kuck et al. |
| 5,938,616 A | 8/1999 | Eaton et al. |
| 6,030,360 A | 2/2000 | Biggs |
| 6,464,645 B1 | 10/2002 | Park et al. |
| 6,979,312 B2 | 12/2005 | Shimada |
| 7,615,044 B2 | 11/2009 | Scheibe et al. |
| 7,691,095 B2 | 4/2010 | Bednarek et al. |
| 7,850,811 B2 | 12/2010 | Hart et al. |
| 7,914,515 B2 | 3/2011 | Heideman et al. |
| 7,955,314 B2 | 6/2011 | Fischer et al. |
| 8,123,703 B2 | 2/2012 | Martin et al. |
| 8,137,308 B2 * | 3/2012 | Schultz ............ A61M 25/0136 600/434 |
| 8,162,934 B2 | 4/2012 | Potter |
| 8,308,659 B2 | 11/2012 | Scheibe et al. |
| 8,323,239 B2 | 12/2012 | Bednarek et al. |
| 8,500,733 B2 | 8/2013 | Watson |
| 8,506,562 B2 | 8/2013 | Anderson et al. |
| 8,603,066 B2 | 12/2013 | Heidman et al. |
| 8,734,699 B2 | 5/2014 | Heideman et al. |
| 9,132,258 B2 | 9/2015 | Bednarek et al. |
| 9,155,865 B2 | 10/2015 | Golden et al. |
| 9,173,642 B2 | 11/2015 | Blaskowski et al. |
| 9,174,024 B1 | 11/2015 | Romoscanu et al. |
| 9,220,868 B2 | 12/2015 | Schultz |
| 9,247,990 B2 | 2/2016 | Kauphusman et al. |
| 9,259,813 B2 | 2/2016 | Heideman et al. |
| 9,492,636 B2 | 11/2016 | Heideman et al. |
| 10,035,000 B2 | 7/2018 | Bednarek et al. |
| 10,130,791 B2 | 11/2018 | Bednarek et al. |
| 2004/0044342 A1* | 3/2004 | MacKay ............ A61B 18/042 606/45 |
| 2005/0288627 A1* | 12/2005 | Mogul ............ A61M 25/0136 604/95.04 |
| 2007/0260225 A1 | 11/2007 | Sakakine et al. |
| 2010/0168827 A1* | 7/2010 | Schultz ............ A61M 25/0136 607/116 |
| 2011/0054287 A1* | 3/2011 | Schultz ............ A61B 5/0422 600/374 |
| 2012/0172703 A1* | 7/2012 | Esguerra ............ A61B 5/062 600/409 |
| 2013/0085492 A1* | 4/2013 | Plascencia, Jr. ... A61B 18/1492 606/41 |
| 2013/0324973 A1* | 12/2013 | Reed ............ A61M 25/0136 604/528 |
| 2014/0039387 A1 | 2/2014 | Kim et al. |
| 2014/0336573 A1 | 11/2014 | Yu et al. |
| 2015/0057610 A1 | 2/2015 | Osypka et al. |
| 2015/0105721 A1 | 4/2015 | Osypka et al. |
| 2015/0196736 A1* | 7/2015 | Tegg ............ A61M 25/0136 604/95.04 |
| 2015/0231366 A1 | 8/2015 | Davies et al. |
| 2015/0335861 A1 | 11/2015 | Osypka et al. |
| 2016/0058974 A1 | 3/2016 | Kimmel et al. |
| 2016/0082226 A1 | 3/2016 | Eversull et al. |

* cited by examiner

STEERABLE GUIDE CATHETER

FIELD OF THE INVENTION

The present technology relates generally to medical devices, systems, and associated methods. More particularly, the present technology relates to devices, methods, and systems for steering a flexible guide catheter or introducer, including, but not limited to, those used in procedures related to treatment of the heart.

BACKGROUND

Many medical procedures require the introduction of specialized medical devices, such as catheters, dilators, and needles, to a target area of the body, such as into the area surrounding the heart. Catheters and access sheaths or introducers have been used for such medical procedures. It is necessary for introducers and catheters to exhibit a degree of flexibility to maneuver through the vasculature of a patient to perform medical procedures. In addition, various configurations of introducers are necessary for the treatment of different conditions or body areas. Handles are often affixed to such devices to enable a physician or practitioner to manipulate the catheter as it is inserted and advanced into the patient. Different handles are required, however, to accommodate the many different preferences of medical practitioners.

DESCRIPTION OF EMBODIMENTS

Figure 1:
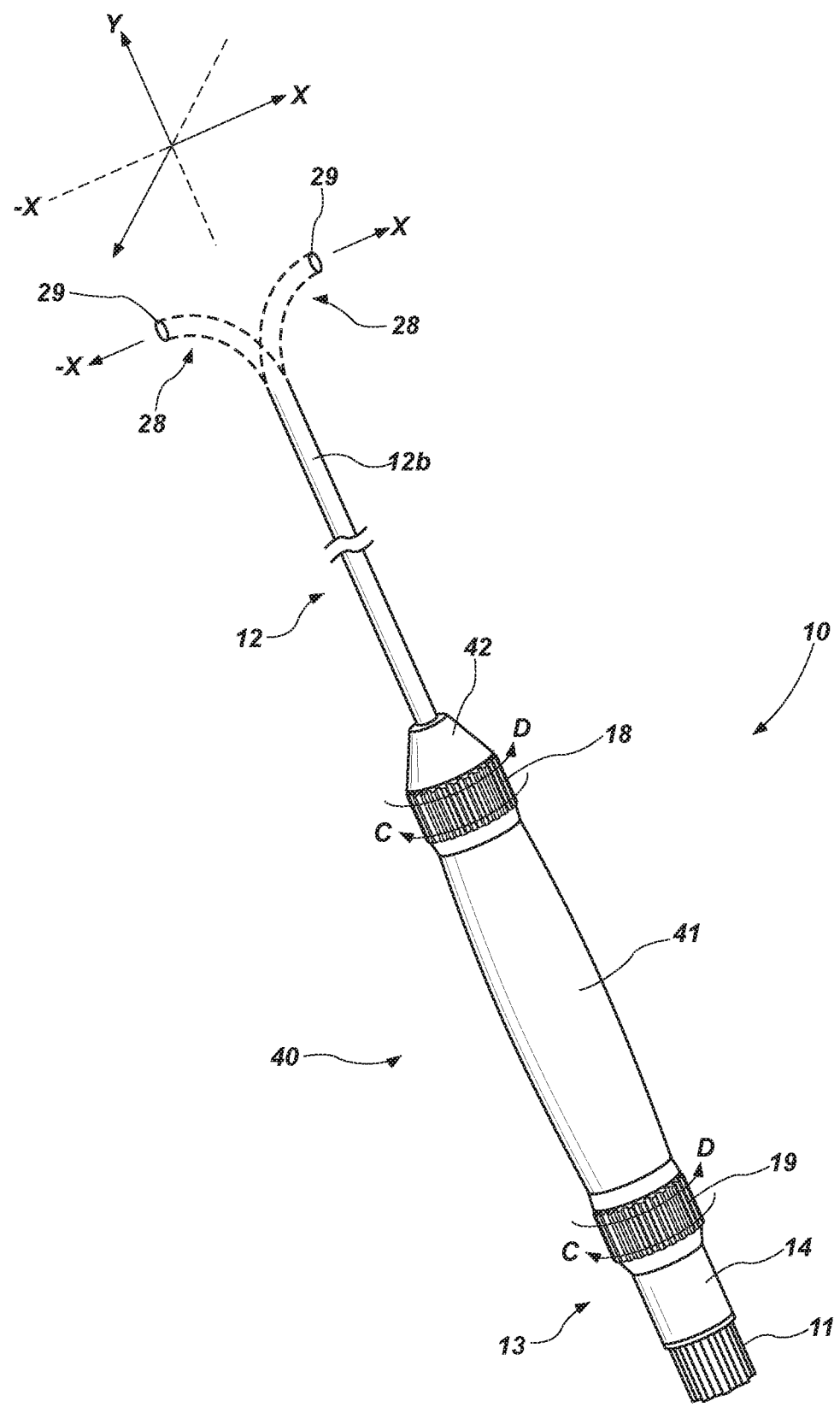
FIG. 1 is a perspective view of a steerable guide catheter in accordance with one aspect of the technology.

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this written description, the singular forms "a," "an" and "the" include express support for plural referents unless the context clearly dictates otherwise. Thus, for example, reference to "a layer" includes a plurality of such layers.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this written description, it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in an electrical or nonelectrical manner. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms."

As used herein, the term "tensioning line" is used to describe any number of devices or mechanisms by which a force is applied to a portion of a guide tube. The force may be applied as a result of a "pulling" force exerted on a connector or wire extending from the distal end of the guide tube to a proximal end of the guide tube, a "pushing" force, the result of deformation of a connector or wire in the distal end of the guide tube due to a change in temperature, etc. or any other means whereby a flexible element disposed within the distal end of the guide tube exerts a flexing or tensioning force on portion of the guide tube.

The term "guide catheter" is used herein to describe any number of guiding elements used to place a "treating catheter" or "treating instrument" into a patient. In one aspect, the guide catheter is removed before treatment of the patient begins and the treating catheter remains in the patient. The guide catheter may be a solid guide wire over which the treating catheter is placed or a hollow guide tube through which the treating catheter is placed. In one aspect, after placement of the treating instrument, the guide catheter is removed from the patient. In another aspect, however, the guide catheter remains in place while a treating instrument is advanced to a location within the patient and remains in place while one or more treating instruments (e.g., ablation tool, suturing tool, etc.) are employed by a clinician. At the termination of the procedure, the treating instruments and guide catheter are removed from the patient. While specific mention is made herein to use of the technology in the vasculature of the patient, it is understood that the technology may be employed to advance a guide catheter into any portion of the body.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Reference in this specification may be made to devices, structures, systems, or methods that provide "improved" performance. It is to be understood that unless otherwise stated, such "improvement" is a measure of a benefit obtained based on a comparison to devices, structures, systems or methods in the prior art. Furthermore, it is to be understood that the degree of improved performance may vary between disclosed embodiments and that no equality or consistency in the amount, degree, or realization of improved performance is to be assumed as universally applicable.

Example Embodiments

An initial overview of technology embodiments is provided below and specific technology embodiments are then described in further detail. This initial summary is intended to aid readers in understanding the technology more quickly, but is not intended to identify key or essential features of the technology, nor is it intended to limit the scope of the claimed subject matter.

Broadly speaking, aspects of the current technology operate to improve a medical practitioner's ability to steer a flexible guide catheter within a cavity of a patient. A cavity may include, but is not limited to, a vessel, a canal, a tissue opening, or other opening within the body of the patient. In order advance a catheter into the cavity of a patient, including, but not limited to the vascular system, a catheter must be substantially stiff to move through the vasculature of a patient. That is, while gripping the catheter on its proximal end, the distal end must have sufficient stiffness to not to kink while pushing the proximal end of the catheter when the distal end encounters resistance. A stiff catheter, however, creates patient discomfort and potentially dangerous situations when trying to advance a catheter through circuitous portions of the vasculature. A stiff but steerable guide can be used to navigate a vascular pathway after which a more flexible, comfortable treating catheter can be placed over or through the steerable guide tube. In one aspect, the flexible guide tube has a deflectable distal end with two tensioning lines disposed on opposing sides of the deflectable distal end. The first tensioning line is configured to deflect the distal end of the flexible guide tube in a first direction and the second tensioning line is configured to deflect the distal end of the flexible guide tube in a second direction that is opposite the first direction and in the same plane as the first direction. For example, the tensioning line operates to deflect the distal end of the flexible guide tube in a direction "X" and the second tensioning line operates to deflect the distal end of the flexible tube in a direction "−X," or in the opposite direction.

A proximal end of the flexible guide catheter and the two tensioning lines are coupled to a handle that is configured to be gripped by a medical practitioner to steer and insert the flexible guide catheter into the patient. The practitioner holds the handle while advancing and steering the guide catheter through the vasculature of the patient. Once the guide catheter is advanced to the desired location, the medical practitioner advances the treating catheter or treating instrument through the interior of the guide catheter. The handle may have many forms, but in one aspect, the handle has a medial portion with a longitudinal axis substantially parallel with a distal portion of the flexible guide tube. A first actuator is disposed on a front end of the handle (i.e., proximal the medial section). A second actuator is disposed on a back end of the handle (i.e., distal the medial section). The two actuators each operate to generate tensioning force acting on the first tensioning line and the second tensioning line. Advantageously, the medical practitioner can flex (i.e., deflect or bend) the distal end of the catheter in the same plane of deflection with either hand or both hands employing either the first actuator, the second actuator, or both actuators at the same time. This enhances the practitioner's ability to effectively steer the guide catheter in the patient by optimizing the practitioner's steering options to steer the distal end of the guide catheter in the same plane of movement. In one aspect, the first and second actuators are both coupled to a first drive adapted to pull on the first tensioning line and the second drive adapted to pull on the second tensioning line.

While there are numerous manners to access cavities and/or organs of a patient, including femoral arterial, brachial arterial, or jugular access, in one aspect, the guide catheter may be advanced through a subxiphoid access point to access the thoracic cavity and the heart in particular. Generally, an incision may be made below the xiphoid process overlying the entry site and the linea alba, for instance, may be incised to obtain the subxiphoid access. The guide catheter may be introduced through the incision and superiorly into the thoracic cavity until the distal tip of the guide catheter is adjacent to the pericardial sac of the heart. Once desirably positioned, the working or surgical theater is assessed and the clinician is free to advance a treating catheter or other treating tool about (i.e., over the guide or through an internal lumen) the guide catheter.

Figure 2A:
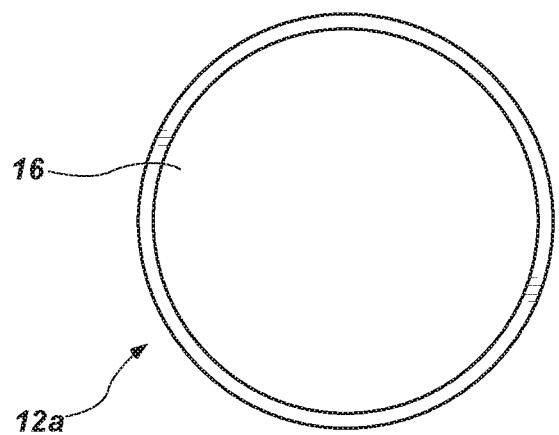
FIG. 2A is a cross-sectional view of a guide tube in accordance with one aspect of the technology.
Figure 2B:
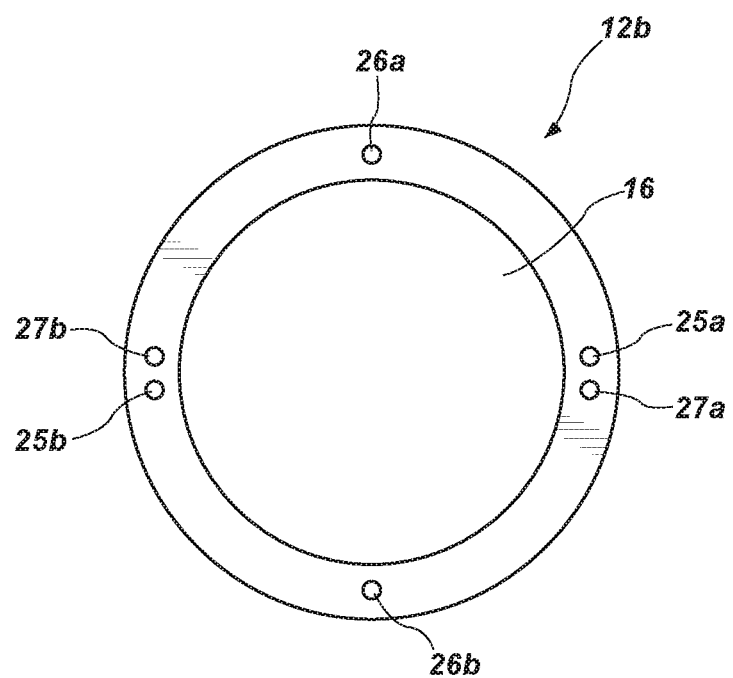
FIG. 2B is a cross-sectional view of a guide tube in accordance with one aspect of the technology.

FIGS. 1, 2A and 2B show a steerable guide catheter 10 in accordance with one aspect of the present technology. The guide catheter 10 comprises a deflectable guide tube 12 with an internal lumen 16 carried by a handle 40 that houses at least a portion of the proximal end of the guide tube 12 therein. In the aspect shown in FIG. 1, the handle 40 is adapted to house a steering mechanism described in greater detail below. Distal (or front) actuator 18 and proximal (or back) actuator 19 comprise a dial and internal components that can be rotationally manipulated in opposing directions as indicated by arrows C and D. The actuators are disposed at opposing ends of the handle 40, either in front of or behind a medial portion 41 of the handle 40. The actuators are coupled to a steering mechanism such that together the actuators and the steering mechanism components comprise a steering assembly. In one aspect, the steering mechanism comprises first and second tensioning lines 20 disposed within the housing 40 and comprise, for example, a cord, a Kevlar line, a control wire, or other line made from metallic or non-metallic materials. The tensioning lines 20 are coupled to the guide tube 12 such that a tension force (e.g., pulling) acting on the tensioning lines operates to flex the guide tube 12.

FIG. 2A shows a cross section of the guide tube 12a when the guide tube 12 is within handle 40 in accordance with one aspect. FIG. 2B shows a cross section of the guide tube 12b when the guide tube 12 is outside the handle 40 in accordance with one aspect of the technology. A portion, however, can also be within the handle as the guide tube 12 transitions form outside the handle 40 to inside the handle 40. The tensioning lines 20 travel substantially an entire length of the guide tube 12b to the distal end portion 28 to couple with a steering mechanism inside the handle 40. More particularly, the tensioning lines 20 travel within a secondary lumen 25a and 25b (shown on FIG. 2B) or another dedicated lumen through the guide tube 12b when outside handle 40 and are disposed about an exterior of the guide tube 12a when inside the handle 40. That is, tensioning lines 20 transition from outside the guide tube 12a to inside the guide tube 12 and into secondary lumens 25a, 25b when the guide tube 12 extends outside the handle 40 through the nose 42 of the handle 40. In one aspect, the guide tube 12b comprises an exterior diameter that is greater when outside of handle 40 than when guide tube 12a is inside handle 40, while the interior diameter of the guide tube 12a and 12b remains the same regardless. In one aspect, the flexible guide tube 12 may be constructed, for example, by extrusion using standard flexible, medical grade plastic materials or by other means and other materials as is known in the art. The guide tube 12, while flexible, may have a plastic memory or bias that normally orients the distal end portion 28, sometimes called the distal end region 28, of the guide tube 12 in an essentially straight configuration. The steering mechanism is used to enable greater control of the orientation of the distal end portion 28 even if a plastic memory or bias is used to resist a deflected distal region. For example, in one aspect, once deflected to a desired configuration, actuators 18, 19 can be locked in place to maintain a particular guide tube 12 geometry.

The handle 40 is sized to be conveniently held by a clinician, and is sized to introduce the guide tube 12b into an interior body region that has been targeted for treatment. The handle 40 may be constructed, for example, from molded plastic, though other materials and types of manufacturing are contemplated and known to persons of ordinary skill in the art. In operation, the steering mechanism is actuated by actuators 18 and 19 to deflect the distal end portion 28 of guide tube 12b out of its essentially straight configuration and into a bent or deflected configuration, as shown in FIG. 1. This is accomplished by the tensioning lines 20 which are coupled to guide tube 12b at (or adjacent) the distal end portion 28 and are tensioned by the steering mechanism to provide a force that deflects the distal end portion 28 of guide tube 12b. In one aspect, the steering mechanism is adapted to hold the distal end portion 28 of the guide tube 12b in its deflected condition, thereby maintaining a treating tool placed within the guide tube 12b in its desired relationship during use. The steerable guide tube 12b obviates the need to equip the treating tool with an on-board steering mechanism or a guide wire lumen. Advantageously, the actuators 18 and 19 each control the tensioning lines 20. The clinician can therefore move the distal end portion 28 of guide tube 12 in the same plane of movement from either the distal or proximal end of the handle 40. This optimizes the operator's ability to advance/operate the guide tube 12 with either hand (left or right hand). This is particularly useful when advancing a treatment catheter or operating a treatment tool with one hand while holding and/or operating the guide catheter 10 with the other hand.

In one aspect of the technology, the proximal end of the guide tube 12a comprises hemostasis or backflow check seals or valves to prevent blood loss and retrograde flow of air into the circulatory system. A hub 14 is disposed on the proximal end of the handle 40 and comprises such a hemostasis seal. The seal comprises an annular soft elastomeric gasket that seals against catheters, instruments, and the dilator, inserted therethrough. The seal can further comprise a valve such as a stopcock, one-way valve such as a duckbill or flap valve, or the like to prevent significant blood loss and air entry when an instrument or catheter is removed from the lumen 16 of the guide catheter 10. The soft annular seal can further comprise a mechanism to compress the inner diameter of the seal radially inward, such as the mechanisms found on Tuohy-Borst valves. In one aspect, the hub 14 further comprises one or more sideports for injection of contrast media such as Omnipaque, Renografin, or other Barium-loaded solutions, for example, or anticoagulant solutions such as heparin, coumadin, persantin, or the like, or for the measurement of pressure at or near the distal end 28 of the guide catheter 10, though fluids may be injected directly through the valve in the hub 14. In one aspect, a plurality of hemostasis valves and/or fluid input connectors or ports or disposed about the hub. In one aspect, the hub 14 comprises a central lumen 15 coupled directly to a Tuohy-Borst valve 11 integrally formed with the hub 14. The lumen of the hub 14 is coupled to the lumen 16 of the guide tube 12 or comprises the proximal end of the guide tube 12 itself. In one aspect, a hemostasis adapter is inserted through the Tuohy-Borst valve. The hub 14 comprises a large diameter Tuohy-Borst valve 11, which can have a capacity ranging from 10 to 30 French (though other much smaller valves, 5-9 French, for example, may be used). Such large Tuohy-Borst valves may not seal fully on closure, or it may not seal at all unless it surrounds a tube larger than 5 or 6 French, for example. The hemostasis adapter can be inserted into such a Tuohy-Borst valve 11 and the Tuohy-Borst valve 11 tightened to obtain a seal around the hemostasis adapter tubing, which can range in diameter from 5 to 10 French. In one aspect, the Tuohy-Borst valve 11 can seal around and allow passage of tubing ranging from 6 to 18 French in diameter. The enlargement can pass through the Tuohy-Borst or other valve but with increased force, which can be relieved once the enlargement can be past the valve. The enlargement also helps prevent inadvertent withdrawal of the hemostasis adapter from the hub 14. In one aspect, a stopcock and purge line can be used for aspiration of blood or saline or the purging of air from the hub lumen.

In one aspect of the technology, the distal end 28 of the guide tube 12 comprises radiopaque markers to denote the beginning and end of the deflecting regions of the catheter. The guide catheter 10 can comprise radiopaque materials such as gold wire, platinum wire, tantalum wire, or coatings of the aforementioned over a malleable, stainless steel, deformable reinforcing layer. The radiopaque materials may also comprise hybrid metallic polymer materials. Such radiopaque markings are especially useful insofar as they allow the operator to more clearly visualize the extent to which the guide catheter 10 is properly placed and/or the extent to which the distal end 28 of the guide tube 12 has been deflected by the operator. In one aspect, a radiopaque marker band is affixed to the distal end 28 of the guide catheter 10 substantially near the distal tip 29 so that the position of the distal tip 29 can be observed and controlled relative to the wall of the left atrium, other cardiac structures, or other portions of the body. This radiopaque marker band can be a non-expandable, axially elongate tubular structure that is coupled to the guide tube 12. The radiopaque marker bands can further be configured to appear different under fluoroscopy by using different shapes and/or types of materials for different bands. Yet another configuration of radiopaque marker bands can be achieved by using malleable wire windings or nano-sized particles of gold, tantalum, platinum alloys, or the like, which are embedded within the guide tube 12.

Figure 3:
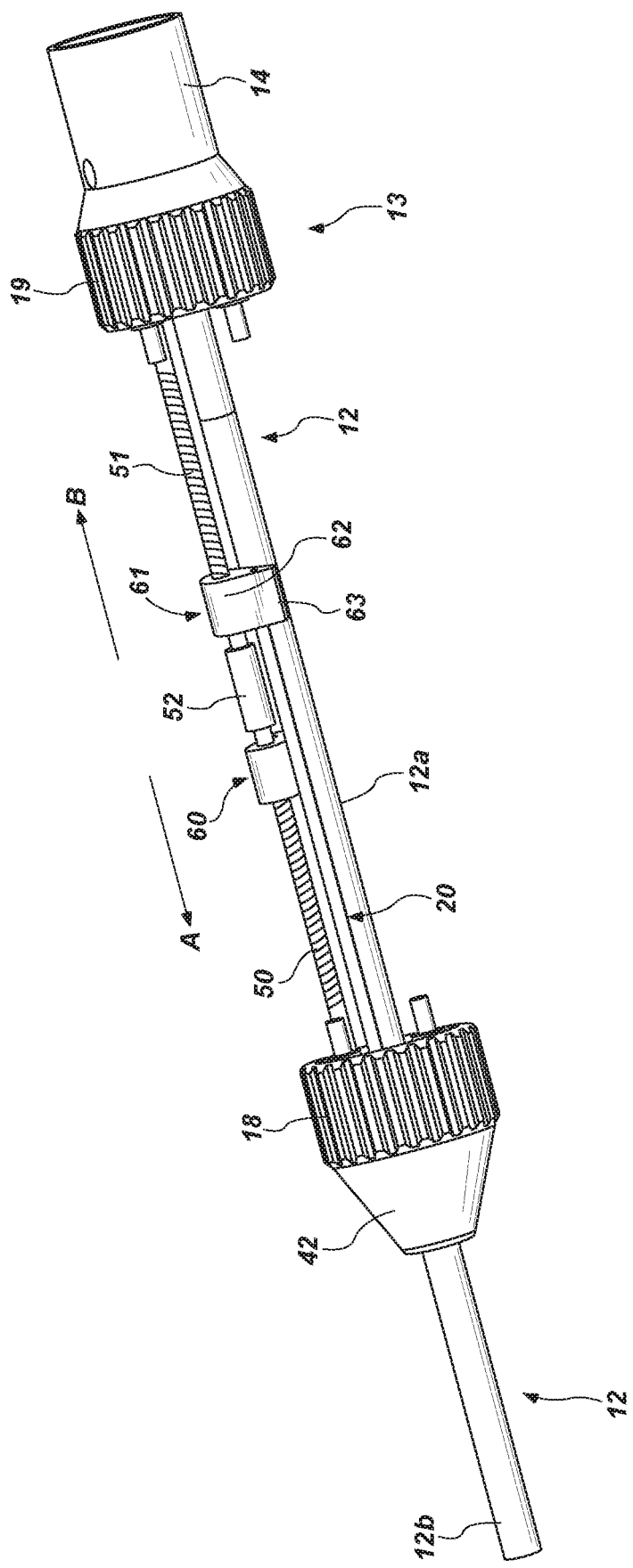
FIG. 3 is a side view of a portion of a steerable guide catheter with a portion of the housing removed in accordance with one aspect of the technology.
Figure 4:
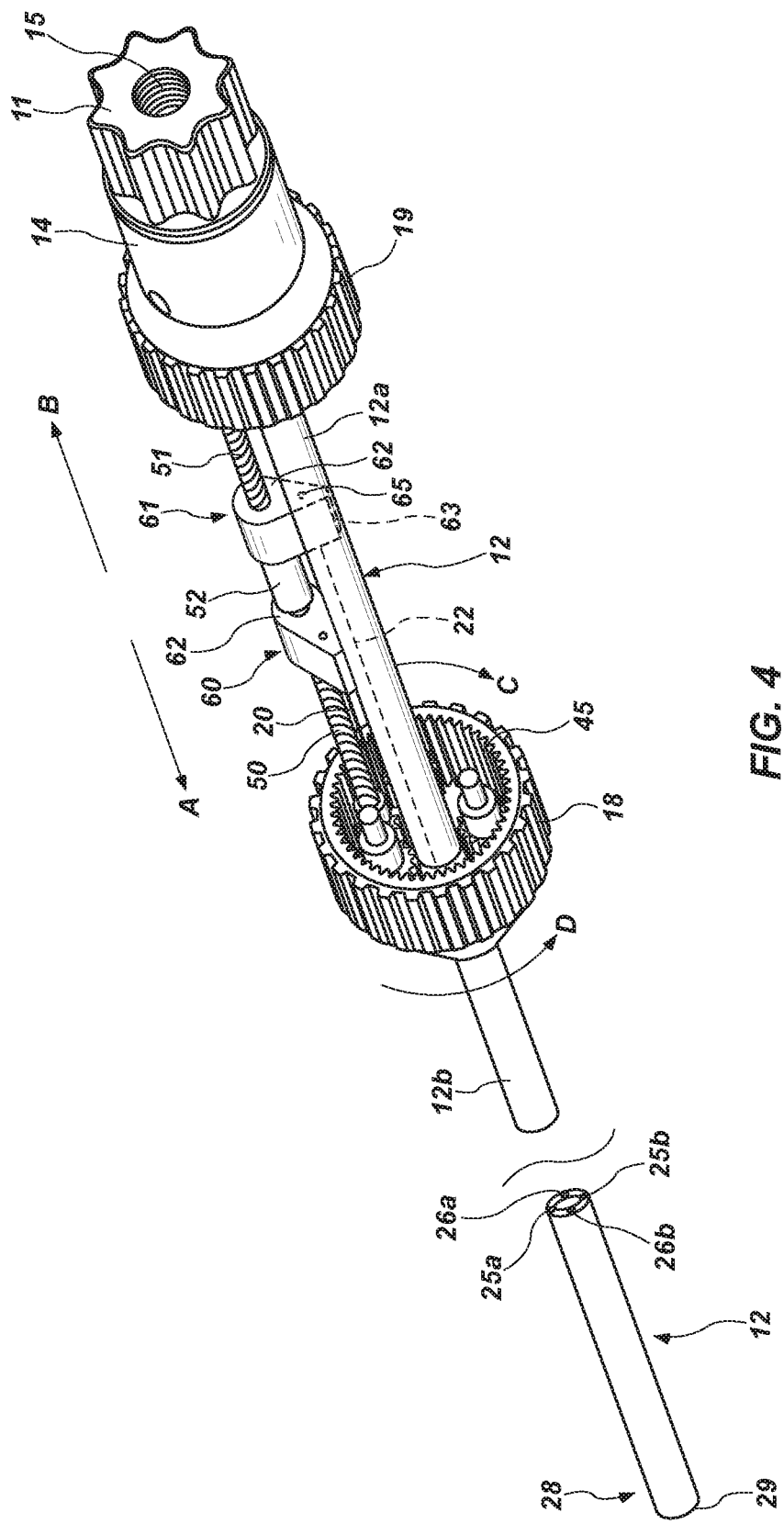
FIG. 4 is back perspective view of a steerable guide catheter with a portion of the housing removed in accordance with one aspect of the technology.
Figure 5:
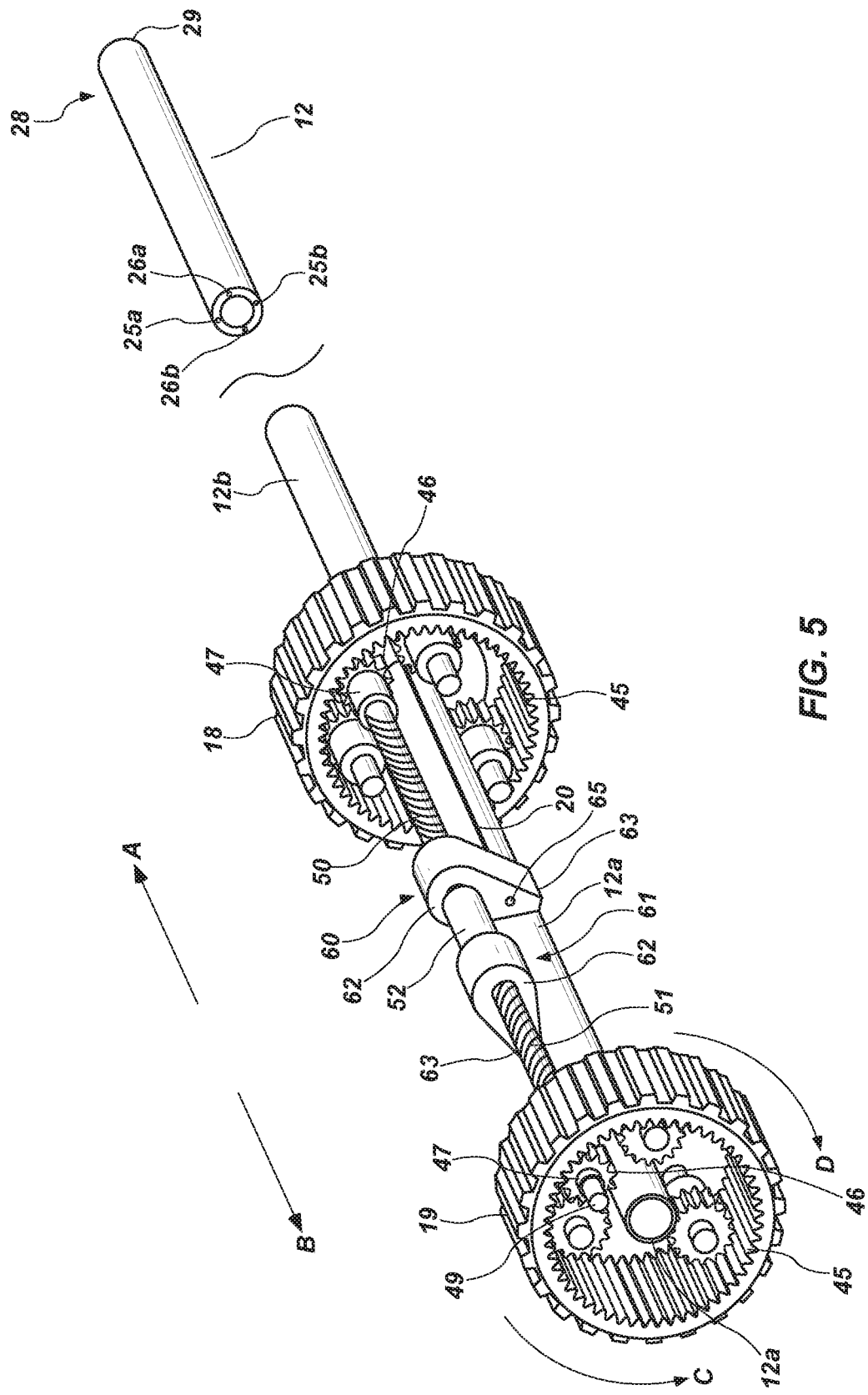
FIG. 5 is a back perspective view of a steerable guide catheter with a portion of the housing and valve removed in accordance with one aspect of the technology.

FIGS. 3-5 disclose components of the steering mechanism in accordance with one aspect of the technology with portions of the housing removed. Different components of the handle 40 are not shown in order to illustrate aspects of the steering assembly within the handle 40. In one aspect, the steering assembly comprises first and second actuators 18, 19. The actuators each include internal teeth 45 that are adapted to mate with teeth 46 of gear 47. Gear 47 is disposed about opposing sides of linear drive shaft 49 that is configured for rotation and translation relative to the actuators. The drive shaft 49 comprises a first set of spiraled threads 50 with a pitch oriented in a first direction and a second set of spiraled threads 51 having a pitch oriented in a second direction and a shaft hub 52 disposed in the center of the shaft 49 and between the first and second set of spiraled threads. A first drive 60 (also referred to herein as a drive nut) and second drive 61 are disposed about opposing sides of the linear drive shaft 49. Each of the first and second drive nuts comprise an aperture within the main body 62 with internal threads adapted to mate with the threads 50, 51 of the shaft 49. The drive nuts 60, 61 further comprise a tab or wing portion 63 extending away from the main body 62 such that wings 63 of the respective drive nuts 60, 61 are on opposing sides of the guide tube 12 inside handle 40. The drive nuts 60, 61 are configured to mate with tensioning lines 21 and 22 that also extend longitudinally about opposing sides of the guide tube 12 to a distal end 28 of guide tube 12. In one aspect, the tensioning lines 21, 22 are coupled to apertures 65 located within with wing 63 of drive nuts 60, 61, however, the tensioning lines may be soldered, bonded, or otherwise coupled to the drive nuts so long as the linear movement of the nuts translates into linear movement the tensioning lines 21, 22.

As the first 18 or second 19 actuator is rotated, gear 47 is likewise rotated resulting in rotation of linear drive shaft 49. The rotational movement of the linear drive shaft 49 translates into linear movement of the drive nuts 60, 61 about drive shaft 49. In one aspect, the respective pitches of the first and second spiraled threads 50, 51 are substantially the same even though they are oriented in different directions. That is, as the drive shaft 49 is rotated, drive nuts 60, 61 will travel the same linear distance about the shaft 49. However, because the direction of the pitch of the first and second threads are oriented in opposite directions (i.e., one is a left-handed thread while the other is a right-handed thread) the direction of the linear travel of the respective drive nuts will be in opposite, but parallel directions as shown by arrows A and B. Consequently, a tensioning force will act upon tensioning lines 21, 21 respectively depending on the direction of rotation of actuators 18 and 19. When rotated in direction C, for example, drive nut 60 may move in the direction B (i.e., towards the proximal end of the handle 40) resulting in a tensioning force acting on tensioning line 21. At the same time, drive nut 61 is moved in direction A (i.e., away from the proximal end of the handle 40) provide slack in the tensioning line 22. Likewise, when the actuators 18 and 19 are rotated in direction D, drive nut 61 is moved in direction B and drive nut 60 is moved in direction A.

In accordance with one aspect of the technology, a second drive shaft is enclosed within the cavity of handle 40 and coupled to a second set of actuators. The second drive shaft is coupled to third and fourth drive nuts that operate to create a tensioning force in the third and fourth tensioning lines. In one aspect, the third and fourth drive nuts are off-set from the first and second drive nuts 60, 61 about the circumference of the guide tube 12 by 90 degrees. In this manner, third and fourth tensioning lines that extend longitudinally about the length of the guide tube 12 through secondary lumens 26a and 26b and are operated by movement of the third and fourth drive nuts and function to flex the distal end 28 of the guide tube 12b in a Y and −Y direction. In other words, while the first and second tensioning lines flex the distal 28 of guide tube 12 in a single plane of movement (i.e., an imaginary X and −X direction), the third and fourth tensioning lines function to flex the distal end 28 of the guide tube 12 in an additional plane of movement (i.e., an imaginary Y and −Y direction). While a 90 degree off-set has been referenced herein, it is understood that the third and fourth tensioning lines can be oriented to deflect the distal end 28 of the guide tube 12 in any other plane off-set from the plane of operation associated with the first and second tensioning lines. For example, in one aspect of the technology, the third and fourth tensioning lines are off-set from the plane of operation associated with the first and second tensioning lines by 15 degrees, 30 degrees, 45 degrees, or 60 degrees. The tensioning lines may also be off-set at other orientations that lie between 1 and 89 degrees as suits a particular application.

In another aspect of the technology, the third and fourth tensioning lines are directed through secondary lumens 27a and 27b. Secondary lumens 27a and 27b (which may also be called tertiary lumens or quaternary lumens) are disposed adjacent lumens 25a and 25b but terminate at a pre-determined distance away from the tip 29 of the distal end 28 of guide tube 12. In this manner, the third and fourth tensioning lines operate to flex the guide tube in substantially the same direction (and hence the same operating plane) as the first and second tensioning lines 50, 51. However, because the lumens 27a and 27b (and consequently the third and fourth tensioning lines) terminate a distance away from the distal end 28, the flexing action occurs a greater distance away from the distal tip 29 than the flexing that results from operation of the first and second tensioning lines. It is understood that numerous tensioning lines can be used in the same secondary lumen (25a, 25b, 26a, 26b, 27a, and 27b) if desired, a single tensioning line can be used in each secondary lumen, or a one or more pairs of tensioning lines may be used in one or more secondary lumens.

In accordance with one aspect of the technology, similar to the first linear drive shaft 49, the second drive shaft comprises threads oriented in opposing directions. Likewise, the opposing threads have a similar pitch so that the distance of linear travel of the associated drive nuts is equivalent even though the direction of the travel is in opposite directions. However, in one aspect, the threads of the second linear drive shaft have a pitch that is more shallow (i.e., having a lighter or less angled pitch) than the pitch of the threads on the first linear drive shaft. A lighter or shallower pitch results in smaller linear travel with the same amount of rotation of the drive shaft. In this manner, the clinician can place the distal end 28 of the guide tube 12 in a "rough" location by using the first set of actuators 18, 19 and the first linear drive shaft 49 and switch to the second set of actuators and the second drive shaft to flex the distal end 28 of guide tube at smaller intervals for more precise movements. In this aspect of the technology, the third and fourth tensioning lines can terminate at the same longitudinal location as the first and second tensioning lines.

Reference has been made herein to aspects of the technology where third and fourth actuators operate a second linear drive shaft. However, in one aspect of the technology, first 18 and second 19 actuators are configured to operate the first linear drive shaft 49 and the second linear drive shaft. As shown in FIGS. 3-5, the actuators 18 and 19 comprise a plurality of internal teeth that mate with the teeth 46 of gear 47 of drive shaft 49. When either actuator 18 or 19 is rotated, the drive shaft 49 is also rotated. In one aspect of the technology, the second drive shaft also comprises a gear with teeth configured to mate with actuator 18 and 19. However, the gears of the second drive shaft are longitudinally off-set from the actuators 18 and 19. That is, in one aspect, the gears associated with the second drive shaft are slightly closer to the center of the second drive shaft than the gears 47 located on the first drive shaft. The actuators 18 and 19 are disposed about the handle such that they are longitudinally biased to engage gear 47 of drive shaft 49. However, the actuators may slide on the handle longitudinally inward towards the medial portion 41 of the handle 40 thereby engaging the gears of the second drive shaft. In this manner, the same set of actuators may be used to drive a plurality of different tensioning lines, whether the different (e.g., the third and fourth) tensioning lines operate in the same plane as the first and second tensioning lines, or in a different plane (e.g., the Y and −Y plane, etc.).

Reference has been made herein to a pulling force on tensioning lines. However, it is understood that a number of different mechanisms may be employed to create tension in the tensioning lines without departing from the scope of the disclosed technology. For example, the tensioning lines may comprise a shape memory alloy (e.g., Nitinol) that is biased in a straight or linear configuration but when subjected to an electrical signal or charge, will flex into a pre-determined configuration. In this aspect, an actuator disposed on a proximal end of the handle 40 would function to flex the distal end 28 of guide tube 12 in both the X and −X directions. Likewise, a second actuator disposed on a distal end of the handle 40 would operate the same tensioning lines associated with the proximal actuator and function to flex the distal end 28 of guide tube 12 in both the X and −X directions.

Certain aspects of the technology include methods of flexing a distal end 28 of a guide tube wherein a clinician displaces either (or both) a first or second actuator 18, 19 disposed about a handle 40 of the steerable guide catheter 10. The steerable guide catheter 10 comprises a flexible guide tube 12 having a deflectable distal end 28 and a proximal end housed within a cavity of a handle 40. First and second drive nuts 60, 61 are disposed about a linear drive shaft 49 within the handle 40, the first drive nut 60 being coupled to a first tensioning line 21 and the second drive nut 61 being coupled to a second tensioning line 22. The first and second tensioning lines are disposed on opposing sides of the flexible guide tube 12 and extend longitudinally along the guide tube 12 to its distal end 28. The method further comprises displacing the first drive nut 60 in a first direction while simultaneously displacing the second drive nut 61 in a second direction, wherein the first direction is opposite and parallel the second direction. In one aspect of the technology, the linear distance of displacement of the first drive nut 60 is substantially equivalent to the linear displacement of the second drive nut 61. The method further comprises displacing the first tensioning line 21 when the first drive nut 60 is displaced in the first direction and displacing the second tensioning line 22 in the first direction when the second drive nut 62 is displaced in the first direction thereby deflecting a distal end of the flexible guide tube 12. In one aspect, the first and second drive nuts 60, 61 are both displaced linearly about the linear drive shaft 49 by displacing either the first 18 or second actuator 19.

It is noted that no specific order is required in these methods unless required by the claims set forth herein, though generally in some embodiments, the method steps can be carried out sequentially.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A steerable guide catheter comprising:
   a flexible guide tube having a deflectable distal end;
   at least first and second tensioning lines coupled to the deflectable distal end of the flexible guide tube, the first tensioning line being configured to deflect the distal end of the flexible guide tube in a first direction and the second tensioning line being configured to deflect the distal end of the flexible guide tube in a second direction that is opposite the first direction; and
   a handle having a distal end coupled to the flexible guide tube, said handle comprising:
      a medial portion having a longitudinal axis substantially parallel with at least a portion of the flexible guide tube;
      a first actuator disposed at a first end of the handle; and
      a second actuator disposed at a second end of the handle opposite the first end,
      wherein the first actuator operates to generate a tensioning force acting on the first tensioning line and the second tensioning line and the second actuator operates to generate a tensioning force acting on the first tensioning line and the second tensioning line,
      wherein the first and second actuators are each coupled to a rotatable gear, said rotatable gear being coupled to a linear drive shaft disposed within an interior cavity of the handle,
      wherein the first and second actuators are both coupled to a first drive adapted to pull on the first tensioning line and a second drive adapted to pull on the second tensioning line, and wherein the first drive and the second drive are disposed about the linear drive shaft, and
      wherein the first drive and the second drive each comprise a drive nut having a through-aperture with a plurality of threads disposed therein, the threads of the drive nuts being configured to mate with threads disposed about an exterior of the linear drive shaft.

2. The steerable guide catheter of claim 1, wherein the first and second tensioning lines extend longitudinally at opposing sides of the flexible guide tube and into the interior cavity of the handle.

3. The steerable guide catheter of claim 1, wherein the threads disposed about the exterior of the linear drive shaft comprise a plurality located on a distal portion of the linear drive shaft and oriented in a first direction and a plurality located on a proximal portion of the linear drive shaft and oriented in a second direction, wherein the first direction of the plurality of threads of the distal portion is opposite the second direction of the plurality of threads of the proximal portion.

4. The steerable guide catheter of claim 1, wherein each drive nut has a tension line coupling disposed about a wing of the drive nut.

5. The steerable guide catheter of claim 1, wherein the through-aperture of the drive nut of the first drive is coupled to the linear drive shaft, the through-aperture of the drive nut of the second drive is coupled to the linear drive shaft, a second aperture of the drive nut of the first drive is coupled to the first tensioning line, and a second aperture of the drive nut of the second drive is coupled to the second tensioning line.

6. A steerable guide catheter comprising:
   a flexible guide tube having a deflectable distal end;
   at least two tensioning lines coupled to the deflectable distal end of the flexible guide tube, wherein a first tensioning line of the at least two tensioning lines is configured to deflect the distal end of the flexible guide tube in a first direction and a second tensioning line of the at least two tensioning lines is configured to deflect the distal end of the flexible guide tube in a second direction; and
   a handle coupled to the flexible guide tube, the handle comprising:
      a first actuator and a second actuator each coupled to a rotatable gear that is coupled to a drive shaft, the drive shaft having thereon a first drive nut and a second drive nut, the first drive nut being coupled to the first tensioning line and the second drive nut being coupled to the second tensioning line,
      wherein both the first actuator and the second actuator are configured to rotate the gear to move both the first and second drive nuts in opposite directions.

7. The steerable guide catheter of claim 6, wherein the first actuator is disposed about a distal end of the handle and the second actuator is disposed about a proximal end of the handle.

8. The steerable guide catheter of claim 6, wherein a proximal end of the flexible guide tube extends through the handle.

9. The steerable guide catheter of claim 6, further comprising a compression fitting disposed about a proximal end of the handle and enclosing a proximal end of the flexible guide tube.

10. The steerable guide catheter of claim 6, further comprising third and fourth actuators disposed about the handle, wherein the at least two tensioning lines comprise third and fourth tensioning lines, and wherein the third and fourth actuators are coupled to a second drive shaft located within the handle and are configured to operate the third and fourth tensioning lines, said third and fourth tensioning lines being configured to deflect the distal end of the flexible guide tube in third and fourth directions, respectively.

11. The steerable guide catheter of claim 6, wherein the first and second tensioning lines are longitudinally disposed at opposing sides of the flexible guide tube.

12. The steerable guide catheter of claim 6, wherein the first drive nut comprises a plurality of threads configured to mate with a first plurality of threads on a first end of the drive shaft and the second drive nut comprises a plurality of threads configured to mate with a second plurality of threads on a second end of the drive shaft.

13. The steerable guide catheter of claim 12, wherein the first plurality of threads on the first end of the drive shaft are oriented in a first direction and the second plurality of threads on the second end of the drive shaft are oriented in a second direction, the first direction being opposite the second direction.

14. The steerable guide catheter of claim 13, wherein a pitch of the first plurality of threads is equivalent to a pitch of the second plurality of threads.

15. The steerable guide catheter of claim 6, wherein each of the first and second drive nuts comprise a first end having a first thickness tapering to a second end having a second thickness smaller than the first thickness.

16. The steerable guide catheter of claim 15, wherein the second end of the first drive nut and the second end of the second drive nut are disposed about opposing sides of the flexible guide tube.

17. A steerable guide catheter comprising:
a flexible guide tube having a deflectable distal end;
two tensioning lines coupled to the deflectable distal end of the flexible guide tube extending down a longitudinal length of the flexible guide tube, wherein the tensioning lines are configured to deflect the distal end of the flexible guide tube; and
a handle coupled to the flexible guide tube, the handle comprising:
a rotatable gear coupled to a linear drive shaft;
first and second rotational actuators coupled to the rotatable gear, each rotational actuator configured to induce rotation of the rotatable gear and the linear drive shaft when rotated;
a first drive nut coupled to the linear drive shaft and a first tensioning line of the two tensioning lines; and
a second drive nut coupled to the linear drive shaft and a second tensioning line of the two tensioning lines,
wherein, when the first or second rotational actuators are rotated, the first drive nut is linearly displaced about the drive shaft in a first direction and the second drive nut is linearly displaced about the drive shaft in a second direction that is opposite the first direction.

18. The steerable guide catheter of claim 17, wherein the first direction and the second direction are substantially parallel to one another.

19. The steerable guide catheter of claim 17, wherein the linear displacement of the first drive nut is substantially equivalent to the linear displacement of the second drive nut.

20. The steerable guide catheter of claim 17, further comprising a valve disposed within a proximal end of the flexible guide tube.

21. A steerable guide catheter comprising:
a flexible guide tube having a deflectable distal end;
at least first and second tensioning lines coupled to the deflectable distal end of the flexible guide tube, the first tensioning line being configured to deflect the distal end of the flexible guide tube in a first direction and the second tensioning line being configured to deflect the distal end of the flexible guide tube in a second direction that is opposite the first direction; and
a handle having a distal end coupled to the flexible guide tube, said handle comprising:
a medial portion having a longitudinal axis substantially parallel with at least a portion of the flexible guide tube;
a first actuator disposed at a first end of the handle; and
a second actuator disposed at a second end of the handle opposite the first end,
wherein the first actuator operates to generate a tensioning force acting on the first tensioning line and the second tensioning line and the second actuator operates to generate a tensioning force acting on the first tensioning line and the second tensioning line,
wherein the first and second actuators are each coupled to a rotatable gear, said rotatable gear being coupled to a linear drive shaft disposed within an interior cavity of the handle, and
wherein a distal portion of the linear drive shaft comprises a plurality of threads disposed about an exterior of the linear drive shaft oriented in a first direction and a proximal portion of the linear drive shaft comprises a plurality of threads disposed about the exterior of the linear drive shaft oriented in a second direction, wherein the first direction of the plurality of threads of the distal portion is opposite the second direction of the plurality of threads of the proximal portion.

22. The steerable guide catheter of claim 21, wherein the first and second actuators are both coupled to a first drive adapted to pull on the first tensioning line and a second drive adapted to pull on the second tensioning line.

23. The steerable guide catheter of claim 22, wherein the first and second drives each comprise a drive nut, each drive nut having a tension line coupling disposed about a wing of the drive nut.

24. The steerable guide catheter of claim 21, wherein the first and second tensioning lines extend longitudinally at opposing sides of the flexible guide tube and into the interior cavity of the handle.

25. The steerable guide catheter of claim 24, wherein the first and second actuators are both coupled to a first drive adapted to pull on the first tensioning line and a second drive adapted to pull on the second tensioning line, and wherein the first drive and the second drive are disposed about the linear drive shaft.

26. The steerable guide catheter of claim 25, wherein the first drive and the second drive each comprise a drive nut having a through-aperture with a plurality of threads disposed therein, the threads of the first drive nut being configured to mate with the plurality of threads of the distal portion of the linear drive shaft and the threads of the second drive nut being configured to mate with the plurality of threads of the proximal portion of the linear drive shaft.

27. The steerable guide catheter of claim 26, wherein the through-aperture of the drive nut of the first drive is coupled to the linear drive shaft, the through-aperture of the drive nut of the second drive is coupled to the linear drive shaft, a second aperture of the drive nut of the first drive is coupled to the first tensioning line, and a second aperture of the drive nut of the second drive is coupled to the second tensioning line.

28. A steerable guide catheter comprising:
a flexible guide tube having a deflectable distal end;
at least first and second tensioning lines coupled to the deflectable distal end of the flexible guide tube, the first tensioning line being configured to deflect the distal end of the flexible guide tube in a first direction and the second tensioning line being configured to deflect the distal end of the flexible guide tube in a second direction that is opposite the first direction; and a handle having a distal end coupled to the flexible guide tube, said handle comprising:
- a medial portion having a longitudinal axis substantially parallel with at least a portion of the flexible guide tube;
- a first actuator disposed at a first end of the handle; and
- a second actuator disposed at a second end of the handle opposite the first end,
- wherein the first actuator operates to generate a tensioning force acting on the first tensioning line and the second tensioning line and the second actuator operates to generate a tensioning force acting on the first tensioning line and the second tensioning line,
- wherein the first and second actuators are each coupled to a rotatable gear, said rotatable gear being coupled to a linear drive shaft,
- wherein the linear drive shaft is coupled to a first drive adapted to pull on the first tensioning line and a second drive adapted to pull on the second tensioning line, and
- wherein the first and second drives each comprise a drive nut, each drive nut having a tension line coupling disposed about a wing of the drive nut.

29. The steerable guide catheter of claim 28, wherein the first and second tensioning lines extend longitudinally at opposing sides of the flexible guide tube and into an interior cavity of the handle.

30. The steerable guide catheter of claim 28, wherein the linear drive shaft is disposed within an interior cavity of the handle.

31. The steerable guide catheter of claim 28, wherein a distal portion of the linear drive shaft comprises a plurality of threads disposed about an exterior of the linear drive shaft oriented in a first direction and a proximal portion of the linear drive shaft comprises a plurality of threads disposed about the exterior of the linear drive shaft oriented in a second direction, wherein the first direction of the plurality of threads of the distal portion is opposite the second direction of the plurality of threads of the proximal portion.

32. The steerable guide catheter of claim 28, wherein the first drive and the second drive are disposed about the linear drive shaft.

33. The steerable guide catheter of claim 32, wherein each drive nut has a through-aperture with a plurality of threads disposed therein, the threads of the drive nuts being configured to mate with threads disposed about an exterior of the linear drive shaft.

34. The steerable guide catheter of claim 33, wherein the through-aperture of the drive nut of the first drive is coupled to the linear drive shaft, the through-aperture of the drive nut of the second drive is coupled to the linear drive shaft, a second aperture of the drive nut of the first drive is coupled to the first tensioning line, and a second aperture of the drive nut of the second drive is coupled to the second tensioning line.

35. A steerable guide catheter comprising:

a flexible guide tube having a deflectable distal end;

at least two tensioning lines coupled to the deflectable distal end of the flexible guide tube, wherein a first tensioning line of the at least two tensioning lines is configured to deflect the distal end of the flexible guide tube in a first direction and a second tensioning line of the at least two tensioning lines is configured to deflect the distal end of the flexible guide tube in a second direction;

a handle coupled to the flexible guide tube, the handle comprising:
- a first actuator and a second actuator each coupled to a drive shaft, the drive shaft having thereon a first drive nut and a second drive nut, the first drive nut being coupled to the first tensioning line and the second drive nut being coupled to the second tensioning line,
- wherein both the first actuator and the second actuator are configured to move both the first and second drive nuts in opposite directions; and third and fourth actuators disposed about the handle, wherein the at least two tensioning lines comprise third and fourth tensioning lines, and wherein the third and fourth actuators are coupled to a second drive shaft located within the handle and are configured to operate the third and fourth tensioning lines, said third and fourth tensioning lines being configured to deflect the distal end of the flexible guide tube in third and fourth directions, respectively.

* * * * *